(12) United States Patent
Tybinkowski et al.

(10) Patent No.: US 6,337,894 B1
(45) Date of Patent: Jan. 8, 2002

(54) ROTARY BEARING ASSEMBLY FOR CT SCANNER GANTRY

(75) Inventors: Andrew P. Tybinkowski, Boxford; Lidia Nemirovsky, Salem; Michael J. Duffy, Methuen, all of MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/764,797

(22) Filed: Jan. 18, 2001

Related U.S. Application Data

(60) Provisional application No. 60/234,027, filed on Sep. 20, 2000.

(51) Int. Cl.[7] .................................................. A61B 6/03
(52) U.S. Cl. ............................................. 378/4; 378/15
(58) Field of Search .............................. 378/15, 4, 193, 378/205

(56) References Cited

U.S. PATENT DOCUMENTS

| | | | |
|---|---|---|---|
| 4,797,008 A | 1/1989 | Helbig et al. ................... 384/49 |
| 4,798,540 A | 1/1989 | Bernardi ...................... 439/22 |
| 5,012,505 A | 4/1991 | Zupancic et al. ............ 378/130 |
| 5,071,264 A | 12/1991 | Franke et al. ................. 384/501 |
| 5,109,397 A | * 4/1992 | Gordon et al. ................... 378/4 |
| 5,448,608 A | * 9/1995 | Swain et al. .................... 378/4 |
| 5,703,921 A | * 12/1997 | Fujita et al. .................... 378/4 |
| RE36,415 E | 11/1999 | McKenna ....................... 378/4 |
| 5,982,844 A | * 11/1999 | Tybinkowski et al. .......... 378/4 |
| 6,188,743 B1 | * 2/2001 | Tybinkowski et al. .......... 378/4 |

* cited by examiner

Primary Examiner—Drew Dunn
(74) Attorney, Agent, or Firm—McDermott, Will & Emery

(57) ABSTRACT

The present disclosure provides a gantry of a CT scanner. The gantry includes an annular outer support having a radially inwardly facing, continuous circumferencial bearing chamber, an annular drum concentrically positioned within the outer support and having a continuous circumferential bearing lip radially extending into the bearing chamber of the outer support to define two circumferential bearing runs within the bearing chamber, and an annular disk extending radially inwardly from an inner circumferential surface of the drum. The disk is adapted to receive and support computed tomography components. The gantry also includes roller bearings in the bearing runs rotatably supporting the drum within the outer support, such that the drum and the disk are rotatable about a rotation axis of the drum.

20 Claims, 3 Drawing Sheets

ROTARY BEARING ASSEMBLY FOR CT SCANNER GANTRY

This application claim benefit to provisional application No. 60/234,027 filed Sep. 20, 2000.

FIELD OF DISCLOSURE

The present disclosure relates to the field of radiography and, in particular, relates to computer tomography ("CT") scanners. Even more particularly, the present disclosure relates to a rotary bearing assembly for a CT scanner.

BACKGROUND OF DISCLOSURE

A typical CT scanner includes a gantry comprising an annular frame for rotatably supporting an annular disk about a rotation or scanning axis of the scanner. The disk includes a central opening large enough to receive a patient extending along the scanning axis, and the disk is rotated about the patient during a scanning procedure. An x-ray tube is positioned on the disk diametrically across the central opening from an array of x-ray detectors. As the disk is rotated, the x-ray tube projects a beam of energy, or x-rays, along a scan plane, through the patient, and to the detector array. By rotating the x-ray source about the scanning axis and relative to the patient, x-rays are projected through the patient from many different directions. An image of the scanned portion of the patient can then be constructed from data provided by the detector array using a computer of the scanner.

U.S. Pat. No. 5,448,608 to Swain et al., entitled Tomographic Scanner Having Center of Rotation for All Physics, discloses a light-weight, portable X-ray tomography system. The system has an annular frame supporting therein a concentric apertured drum rotatable about a rotational axis. A plurality of components for performing a tomographic scan are mounted on the drum with respect to both sides of a mean plane of the drum so as to be dynamically balanced for rotation with the drum about the rotational axis, and so that the center of the mass moment of inertia, the center of rotation, the center of thermal expansion of the drum and components mounted thereon, and the center of the scanning plane substantially coincident on that rotational axis.

U.S. Pat. No. 5,982,844 to Tybinkowski et al., entitled Computed Tomography Scanner Drive System and Bearing discloses a gantry disk sheaved about its perimeter such that the gantry is operable as a driven pulley rotatable about an object to be scanned. A motor assembly mounted to a stationary frame includes a similar sheaved drive pulley, and a belt is tensioned between the drive pulley of the motor assembly and the driven pulley of the gantry disk to transfer rotational motion of the motor to drive the gantry rotationally about the object. In a preferred embodiment, the belt comprises a V-belt or poly-V-belt. The gantry bearings comprise a pair of wire bearings located between an outer ring frame and inner rings supporting the gantry disk, proximal to the gantry center of mass. The disclosed drive system and bearing provides a simple and effective technique for driving the gantry about the object, providing sufficiently accurate angular positioning in a reliable and cost effective drive system.

What is desired is a CT scanner gantry including all of the benefits of the Swain et al. and Tybinkowski et al. patents, as well as additional benefits.

SUMMARY OF DISCLOSURE

The present disclosure, accordingly, provides a gantry having a novel bearing arrangement for use as part of a CT scanner. The gantry includes an annular outer support, an annular drum concentrically positioned within the outer support, and an annular disk extending radially inwardly from an inner circumferential surface of the drum. The disk is adapted to receive and support computed tomography components.

The annular outer support has a radially inwardly facing, continuous circumferencial bearing chamber, and the drum has a continuous circumferential bearing lip radially extending into the bearing chamber of the outer support to define two circumferential bearing runs within the bearing chamber. The gantry also includes roller bearings in the bearing runs allowing the drum to rotate within the outer support, such that the drum, the disk and computed tomography components supported on the disk are rotatable about a rotation axis of the drum.

According to one aspect, the roller bearings comprise spherical ball bearings, and the gantry also includes bearing wires circumferentially extending within the bearings runs and guiding the roller bearings.

According to another aspect, the drum axially extends between first and second ends, and the bearing lip is equally spaced from the ends, and the annular disk is concentrically aligned with the bearing lip of the drum. Whereby, the bearings are aligned with a center of mass of the gantry.

According to an additional aspect, the disk is adapted to receive x-ray tomography components on both sides of the disk, and to allow at least some of the components to extend through the disk, so that components fixedly mounted on the disk will be substantially balanced for rotation with the disk about the rotation axis.

According to a further aspect, a portion of the radially outermost surface of the rotatable drum is sheaved, and the gantry includes a motor having a sheaved drive pulley, and a belt mounted between the sheaved drive pulley and the sheaved portion of the drum.

The foregoing and other features and advantages of the present disclosure will become more readily apparent from the detailed description of the disclosure, as illustrated in the associated drawings.

DETAILED DESCRIPTION OF DISCLOSURE

As is know to those skilled in the technical art of computed tomography, a patient to be examined is positioned in a scan circle of a computer tomography (CT) scanner, parallel with a scan axis of the scanner, and between an x-ray tube and an x-ray detector array. The x-ray tube then projects x-rays along a scan plane, through the patient, and to the detector array. By rotating the x-ray source about the scan axis and relative to the patient, radiation is projected through the patient from many different directions. An image of the scanned portion of the patient can then be constructed by a computer from data provided by the detector array.

Figure 1:
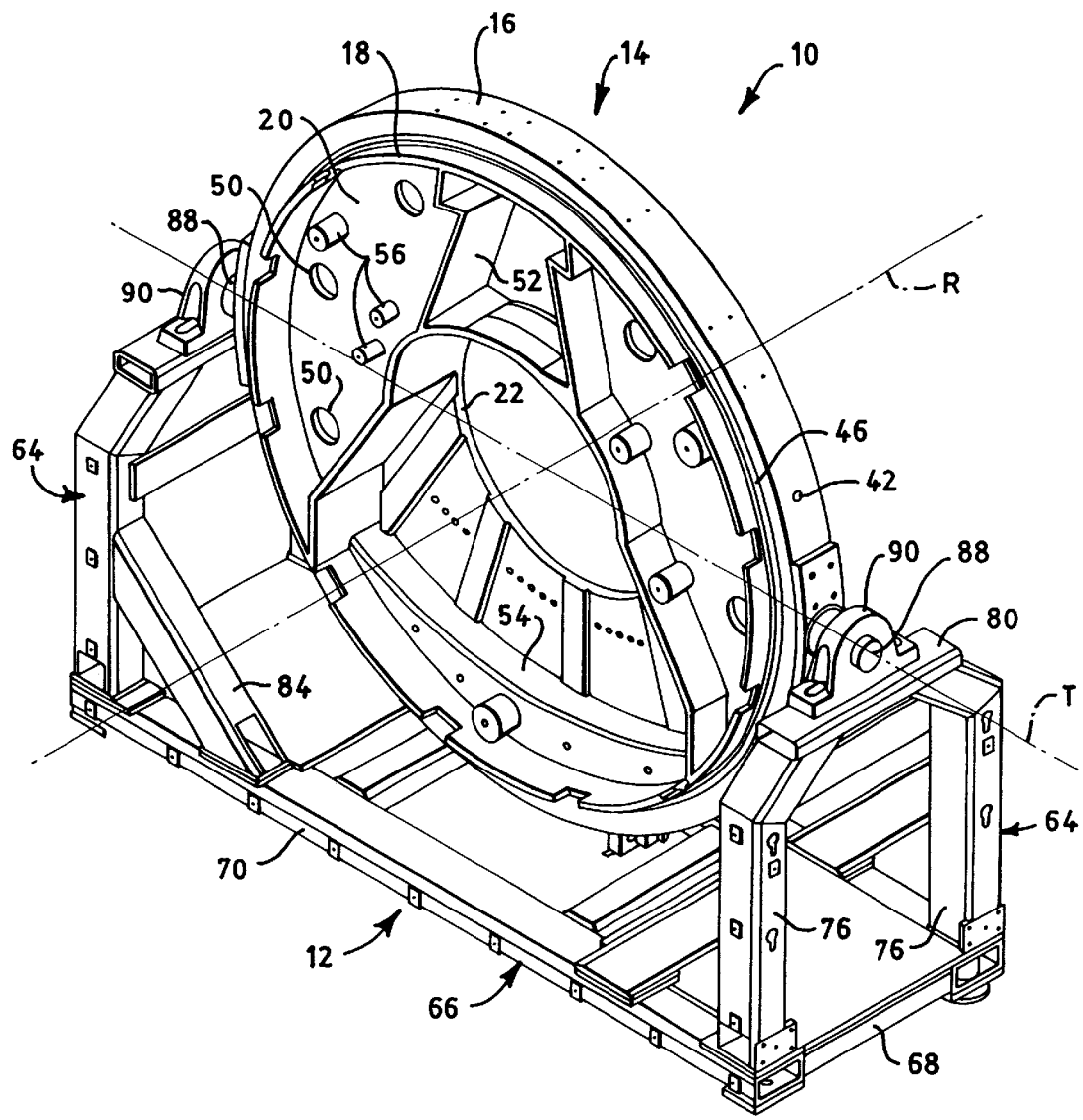
FIG. 1 is a perspective view of a CT scanner frame including an annular gantry constructed in accordance with the present disclosure.

Referring to FIG. 1, the present disclosure provides a frame 10 for a CT scanner, which includes a stand 12 and a gantry 14 mounted to the stand. The gantry 14 is shown in greater detail in FIGS. 2 through 5, wherein like reference characters refer to the same parts throughout the different views. The gantry 14 is provided with a novel bearing arrangement constructed in accordance with the present disclosure. In addition, the gantry 14 is adapted such that components for performing a tomographic scan are mounted on the gantry so as to be dynamically balanced about the rotation axis.

The gantry 14 includes an annular outer support 16, an annular drum 18 concentrically positioned within the outer support 16, and an annular disk 20 extending radially inwardly from an inner circumferential surface of the drum 18. The disk 20 has a central opening 22 for receiving a patient to be scanned, and the disk 20 adapted to receive and support computed tomography components, as discussed in greater detail below.

Figure 3:
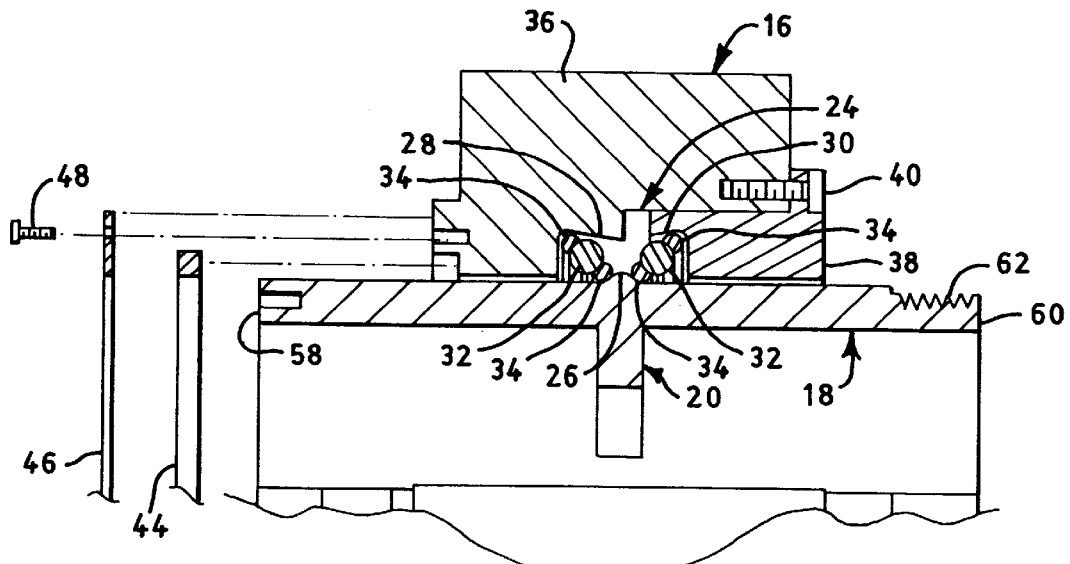
FIG. 3 is an enlarged sectional view of the gantry taken along line 3—3 of FIG. 2.
Figure 4:
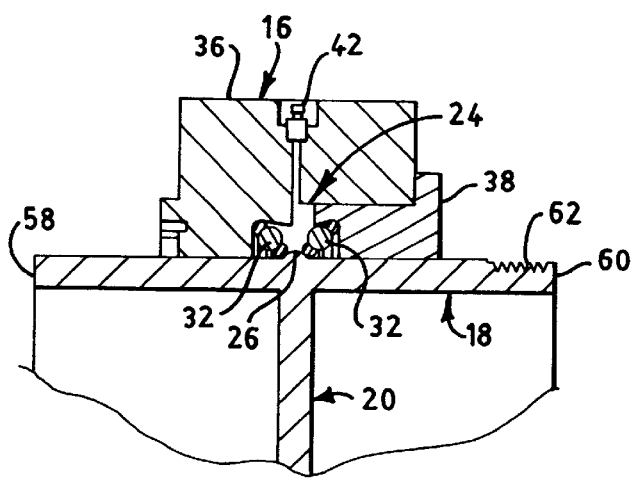
FIG. 4 is an enlarged sectional view of the gantry taken along line 4—4 of FIG. 2.

As shown best in FIGS. 3 and 4, the annular outer support 16 has a radially inwardly facing, continuous circumferential bearing chamber 24, and the drum 18 has a continuous circumferential bearing lip 26 radially extending into the bearing chamber 24 of the outer support 16 to define two circumferential bearing runs 28, 30 within the bearing chamber 24. The gantry 14 also includes roller bearings 32 in the bearing runs 28, 30 allowing the drum 18 to rotate within the outer support 16, such that the drum 18 and the disk 20 (and computed tomography components supported on the disk 20) are rotatable about a rotation axis "R" of the drum 18. The rotation axis "R" of the drum 18 coincides with the scan axis of a CT scanner incorporating the frame.

Preferably, the roller bearings comprise spherical ball bearings 32. Bearing wires 34 are provided and circumferentially extend within the bearing runs 28, 30 and guide the spherical ball bearings. Suspended between the bearing wires 34, the spherical ball bearings 32 glide across the wires with minimal resistance as the drum 18 rotates within the outer support 16. In particular, bearing wires 34 are positioned on either side of the bearing lip 26, and bearing wires are positioned in two circumferential corners of the bearing chamber 24. The bearing arraignment emulates the well-known Franke bearing interface, as disclosed in U.S. Pat. Nos. 4,797,008 and 5,071,264, which are incorporated herein by reference. Ball spacers can be provided between the ball bearings 32 to prevent adjacent balls from contacting or otherwise interfering with each other. The bearings 32 are preloaded according to manufacturer specifications, as described below.

The bearing arrangement of the present invention confers several advantages. First, the bearings 32 and the wire 34 interface operates with less friction than traditional bearing races as the wires provide a smooth and efficient track for the ball bearings. As a result, the bearing arrangement reduces the torque necessary to rotate the drum 18 and the disk 20 within the outer support 16. Also, no custom bearing housing is required, as the bearing runs 28, 30 are provided by the surfaces of the drum 18 and the outer support 16. Furthermore, the bearing arrangement and novel gantry 14 design according to the present disclosure requires fewer parts, are light weight, operate quietly, and are relatively inexpensive.

Figure 5:
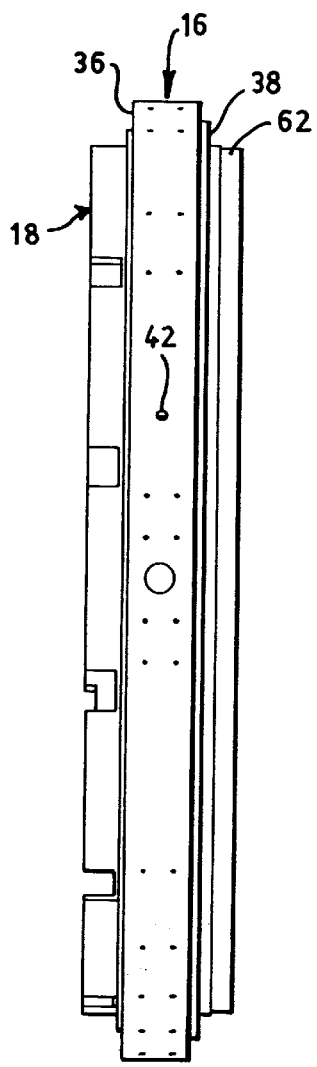
FIG. 5 is a side elevation view of the gantry of FIG. 2.

As shown in FIGS. 2 through 5, the annular outer support 16 preferably is constructed from first and second annular pieces 36, 38 axially joined to define the bearing chamber 24. The pieces 36, 38 are secured together with bolts 40, which pre-load the bearings 32 and are tightened according to the bearing manufacturer's specifications. As shown in FIGS. 1, 4 and 5, the annular first piece 36 includes grease fittings 42 providing communication with the bearing chamber 24 so that the ball bearings 32 can be packed in grease in a convenient manner. As shown in FIG. 3, an annular grease seal 44 is provided between the annular outer support 16 and the annular drum 18, and is held in place by an annular cover 46 secured with fasteners 48.

Figure 2:
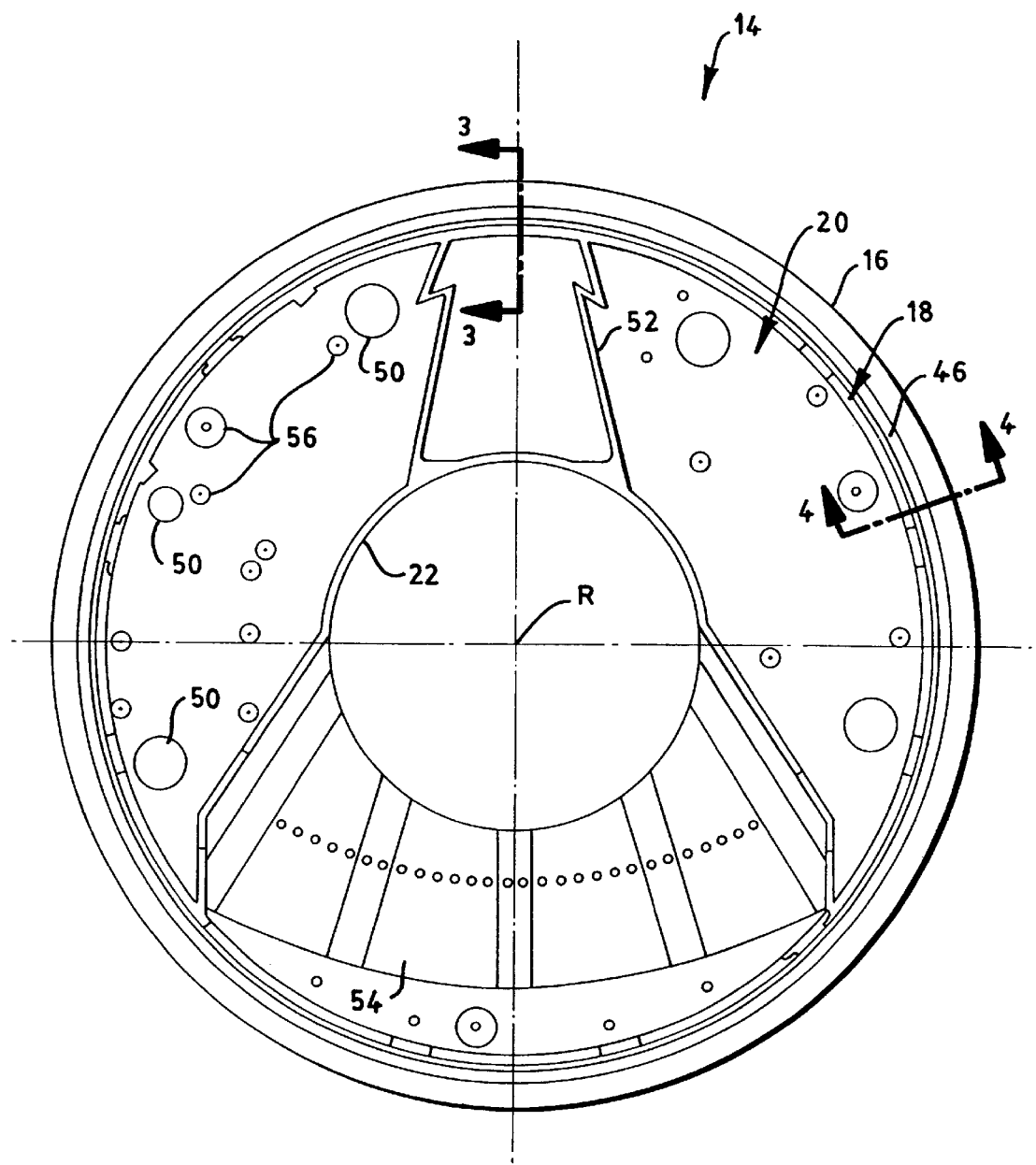
FIG. 2 is a front elevation view of the gantry of FIG. 1.

As shown best in FIGS. 1,2 and 6, the disk 20 is configured with openings 50 and mounting bosses 56 for receiving and supporting conventional x-ray tomography components, and a mounting receptacle 52 for an x-ray source and a mounting receptacle 54 for an x-ray detector array. The components secured to the annular disk 20 will of course rotate with the drum 18 about the rotation axis "R". The disk 20 is preferably adapted such that components mounted thereon will be dynamically balanced about the rotation axis "R" of the disk 20. In particular, the openings 50, the mounting receptacles 52, 54, and the mounting bosses 56 are provided so that components will be mounted on both sides of the disk 20, and at least some of the components, such as the x-ray source and the x-ray detectors will extend through the disk 20, whereby the components can be dynamically balanced about the rotation axis "R" of the disk 20.

Major components of the CT scanner to be mounted on the disk 20 include an x-ray source, a detector array, an x-ray power source including a power converter and batteries, a power source for the detector array, and a control and data handling electronics package. Accordingly, the term "components" as used herein can include not only one or more of these major components, but also any number of elements supported by the disk 20, depending upon the particular design of the CT scanner. For example, a number of minor components in the sense of mass and volume, such as a collimator, a motor driven fan for cooling the x-ray source, anti-scatter plates for the detector array, a detector assembly control panel and/or the like are also typically mounted on the disk 20, and thus can be included in the term "components" as used herein.

The gantry 14 is also adapted so that the weight of the gantry 14 and any components mounted thereon are substantially aligned with the bearings 32. In particular, the drum 18 axially extends between first and second ends 58, 60, and the bearing lip 26 is equally spaced from the ends, i.e., the bearing lip 26 is located at the middle of the drum 18. In addition, the annular disk 20 is concentrically aligned with the bearing lip 26 of the drum 18. By locating the bearings 32 at the center of mass of the gantry 14, a smaller bearing configuration is allowed since the moment arm between the bearings 32 and the center of mass of the disk 20 is minimized, thereby decreasing the radial load and thrust load on the bearings. This, in combination with the mounting of components on both sides of the gantry disk 20, achieves dynamic balancing of the disk 20 relative to the bearings 32, and substantially eliminates cantilevered loading on the bearings 32.

U.S. Pat. No. 5,448,608 to Swain et al., entitled Tomographic Scanner Having Center of Rotation for All Physics, and which is incorporated herein by reference, discloses an x-ray tomography system wherein components are mounted on a drum so as to be dynamically balanced for rotation with the drum about a rotational axis. The scanner disclosed by Swain et al. is also configured so that the center of the mass moment of inertia, the center of rotation, the center of thermal expansion of the drum and components mounted thereon, and the center of the scanning plane substantially coincident on the rotational axis of the drum.

Preferably, the outer support 16, the drum 18 and the disk 20 of the gantry 14 according to the present disclosure are made of the same light-weight, rigid metal such as aluminum, magnesium-aluminum alloy and the like. The drum 18 and the disk 20 are preferably made as a single piece.

Referring to FIGS. 3 through 5, a portion 62 of the radially outermost surface of the rotatable drum 18 is sheaved to interface with longitudinal grooves of a poly-V-belt. The cross-sectional V-shaped geometry of the belt in combination with the large drum 18 circumference serve to minimize belt slippage, maximizing accuracy in rotational disk 20 positioning and rotation rate. The sheaved portion 62 is preferably provided adjacent to the second end 60 of the drum 18. Although not shown, the frame 10 includes a motor and drive pulley system and corresponding belt tensioner such as that disclosed in U.S. Pat. No. 5,982,844 to Tybinkowski et al., which is assigned to the assignee of the present disclosure and incorporated herein by reference.

Referring back to FIG. 1, the stand 12 of the CT scanner frame 10 includes two arms 64 supporting the gantry 14. The outer support 16 of the gantry 14 is pivotally mounted to the arms 64 of the stand 12 for tilting of the gantry 14 about a tilt axis "T" extending between the arms and through the center of the gantry, substantially normal to the rotation axis "R" of the gantry.

The stand 12 is generally of a U-shaped configuration and includes a horizontal base 66 from which the arms 64 extend upwardly from opposite ends of the base. The base 66 is comprised of, for example, various structural members including, end members 68 and front and rear members 70 connected together to form a rectangle. The arms 64 are, for example, each comprised of various structural members including vertical members 76 extending upwardly from the base to a top piece 78. The stand 12 also includes braces 84 extending at an angle between the base 66 and the arms 68 to provide additional strength. The stand 12 is preferably provided with leveling legs or height adjustable rolling means, such as adjustable castors.

Means for pivotally mounting the annular outer support 16 of the gantry 14 to the arms 64 of the stand 12 include cylindrical beams 88 extending radially outwardly from the outer support, and annular bearings 90 secured to the top pieces 80 of the arms and rotatably supporting the beams 88. The tilt axis "T" of the gantry 14 passes through the axes of both beams 88. Preferably, the beams 88 are aligned with the disk 20 of the gantry 14, such that the weight of the gantry 14 and components thereon are aligned with the stand 12.

Other modifications and implementations will occur to those skilled in the art without departing from the spirit and the scope of the disclosure as claimed. Accordingly, the above description is not intended to limit the disclosure except as indicated in the following claims.

What is claimed is:

1. A gantry of a CT scanner comprising:
    a) an annular outer support having a radially inwardly facing, continuous circumferencial bearing chamber;
    b) an annular drum concentrically positioned within the outer support and having a continuous circumferential bearing lip radially extending into the bearing chamber of the outer support to define two circumferential bearing runs within the bearing chamber;
    c) an annular disk extending radially inwardly from an inner circumferential surface of the drum, the disk adapted to receive and support computed tomography components; and
    d) roller bearings contained in the bearing runs rotatably supporting the drum within the outer support, such that the drum and the disk are rotatable about a rotation axis of the drum.

2. A gantry according to claim 1, wherein the drum axially extends between first and second ends, and the bearing lip is equally spaced from the ends.

3. A gantry according to claim 1, wherein the annular disk is concentrically aligned with the bearing lip of the drum.

4. A gantry according to claim 1, wherein the drum and annular disk are unitary.

5. A gantry according to claim 1, wherein the roller bearings comprise spherical ball bearings.

6. A gantry according to claim 1, further comprising bearing wires circumferentially extending within the bearings runs and guiding the roller bearings.

7. A gantry according to claim 6, wherein bearing wires are positioned on either side of the bearing lip, and bearing wires are positioned in two circumferential corners defined by the bearing chamber.

8. A gantry according to claim 1, wherein the annular outer support includes first and second annular pieces axially joined to define the bearing chamber.

9. A gantry according to claim 8, wherein the first and second annular pieces are secured together with preloaded bolts.

10. A gantry according to claim 1, wherein the annular outer support includes grease fittings providing communication with the bearing chamber.

11. A gantry according to claim 1, further comprising an annular seal between the annular outer support and the annular drum.

12. A gantry according to claim 1, wherein the annular disk includes apertures for receiving computer tomography components.

13. A gantry according to claim 1, wherein a portion of the radially outermost surface of the rotatable drum is sheaved.

14. A gantry according to claim 13, further comprising:
    a motor having a sheaved drive pulley; and
    a belt mounted between the sheaved drive pulley and the sheaved portion of the drum.

15. A gantry according to claim 1, further including diametrically opposed mounts extending radially outwardly from the outer support for mounting the gantry on a stand, the mounts aligned with the disk.

16. A CT scanner including a gantry according to claim 1, and further comprising:
    a stand supporting the gantry; and
    x-ray tomography components operatively mounted on the annular disk of the gantry for rotation therewith about the rotation axis.

17. A gantry according to claim 1, wherein the disk is adapted to receive x-ray tomography components on both sides of the disk.

18. A gantry according to claim 1, wherein the disk is adapted to allow at least some of x-ray tomography components to extend through the disk.

19. A gantry according to claim 1, wherein the disk is adapted to so that components fixedly mounted on the disk will be substantially balanced for rotation with the disk about the rotation axis.

20. A gantry according to claim 1, wherein the disk, the drum and the outer support are formed of the same light-weight, rigid metal.

* * * * *